United States Patent [19]

Kondo et al.

[11] Patent Number: 5,371,285
[45] Date of Patent: Dec. 6, 1994

[54] METHOD OF PRODUCING KETO ACIDS

[75] Inventors: Masahiro Kondo; Michio Tanaka; Naoya Sakamoto; Hajime Ooyoshi, all of Yamaguchi, Japan

[73] Assignee: Mitsui Petrochemical Industries, Ltd., Tokyo, Japan

[21] Appl. No.: 38,283

[22] Filed: Mar. 29, 1993

Related U.S. Application Data

[63] Continuation-in-part of Ser. No. 873,220, Apr. 24, 1992, abandoned.

[30] Foreign Application Priority Data

Apr. 25, 1991 [JP] Japan .................................. 3-095901
Mar. 11, 1992 [JP] Japan .................................. 4-052889

[51] Int. Cl.$^5$ ............................................ C07C 229/00
[52] U.S. Cl. .................................................. 562/441
[58] Field of Search ...................................... 562/441

[56] References Cited

U.S. PATENT DOCUMENTS

| | | | |
|---|---|---|---|
| 1,970,908 | 12/1933 | Gubelmann | 562/441 |
| 3,394,165 | 9/1967 | Pecherer | 562/441 |
| 3,455,985 | 7/1969 | Sternbach et al. | 562/441 |

FOREIGN PATENT DOCUMENTS

| | | | |
|---|---|---|---|
| 0065053 | 4/1984 | Japan | 562/441 |
| 1151158 | 7/1986 | Japan | 562/441 |
| 2070350 | 3/1987 | Japan | 562/441 |
| 3190852 | of 1989 | Japan | . |
| 3056452 | 3/1991 | Japan | 562/441 |

*Primary Examiner*—Marianne M. Cintins
*Assistant Examiner*—Keith MacMillan
*Attorney, Agent, or Firm*—Sherman and Shalloway

[57] ABSTRACT

In a method of producing a keto acid having the general formula

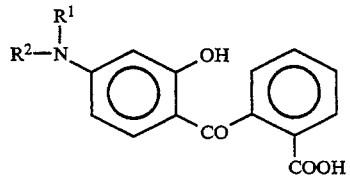

wherein $R^1$ and $R^2$ independently represent an alkyl of 1–6 carbons or a cycloalkyl of 4–8 carbons, by reacting an m-aminophenol having the general formula

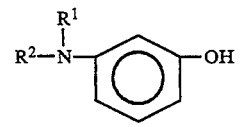

wherein $R^1$ and $R^2$ are the same as above, with phthalic anhydride, in an organic solvent, the improvement comprising effecting the reaction in an amount of the organic solvent which is insufficient to dissolve the keto acid produced in the reaction, so that at least a portion of the resultant keto acid crystallizes out of the solvent and allowing the reaction to proceed in a heterogeneous system.

15 Claims, 1 Drawing Sheet

METHOD OF PRODUCING KETO ACIDS

This is a continuation-in-part application Ser. No. 07/873,220 filed Apr. 24, 1992, now abandoned.

FIELD OF THE INVENTION

This invention relates to a method of producing keto acids.

Keto acids are useful intermediates for the production of fluoran compounds used as dyestuff in pressure- or heat-sensitive recording.

DESCRIPTION OF THE PRIOR ART

The keto acid has hitherto been produced by the reaction of an N,N-dialkyl-m-aminophenol with phthalic anhydride in a homogeneous system in a molar ratio of phthalic anhydride to N,N-dialkyl-m-aminophenol of 0.5–2 both dissolved in an inactive organic solvent such as toluene, xylene or tetrahydrofuran at a temperature of 80°–150° C. However, the method by-produces a considerable amount of Rhodamines known as red dyes by the reaction of the resultant keto acid with the N,N-dialkyl-m-aminophenol, thereby to reduce the yield of the keto acid, as well as to make it difficult to obtain a high purity keto acid. Moreover, the method employs a homogeneous reaction wherein the resultant keto acid is dissolved in a solvent used, and hence the resultant keto acid is usually recovered by alkali extraction. Thus, the method not only requires a large, number of steps of operations, but also produces a large quantity of neutralization waste water.

To solve the above problem regarding the undesirable by-production of Rhodamines, there has been proposed a method in which an aqueous solution of an alkali metal hydroxide such as sodium hydroxide is added to the resultant reaction mixture, the reaction mixture is heated to decompose the by-produced Rhodamines to alkali metal salts of the keto acid, the alkali metal salt of the keto acid is crystallized out and then dissolved again in water, and then the salt is neutralized in water to recover the keto acid, as disclosed in Japanese Patent Application Laid-open No. 62-70350. However, this method also needs a large number of steps, and also produces a large amount of neutralization waste water.

A further method is also set forth in Japanese Patent Application Laid-open No. 59-65053 wherein alkali extraction of the resultant keto acid is not employed. According to the method, after the reaction, a solvent is removed by distillation from the resultant reaction mixture, and then a crystallization solvent is added to the reaction mixture, so that the resultant keto acid is crystallized out of the mixture. However, this method also needs many steps of operations. As a further problem, if the residue solidifies after the removal of the solvent from the reaction mixture, the method may not be applicable to industrial production of the keto acid.

BRIEF SUMMARY OF THE INVENTION

It is, therefore, an object of the invention to provide a method of producing a high purity keto acid in high yields by the reaction of an N,N-dialkyl-m-aminophenol with phthalic anhydride wherein undesirable by-production of Rhodamines is substantially suppressed and the resultant keto acid is recovered or separated by a simple and hence industrially advantageous manner, without resorting to alkali extraction which inevitably produces a large amount of neutralization waste water.

According to the invention, there is provided an improvement in a method of producing a keto acid having the general formula

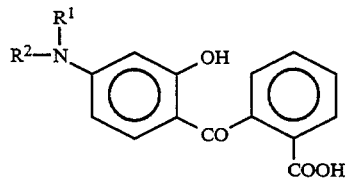

wherein $R^1$ and $R^2$ independently represent an alkyl of 1–6 carbons or a cycloalkyl of 4–8 carbons, by reacting an m-aminophenol having the general formula

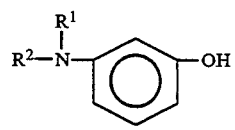

wherein $R^1$ and $R^2$ are the same as above, with phthalic anhydride, in an organic solvent, the improvement comprising effecting the reaction in an amount of the organic solvent which is insufficient to dissolve the keto acid produced in the reaction, so that at least a portion of the resultant keto acid crystallizes out of the solvent and allowing the reaction to proceed in a heterogeneous system.

DETAILED DESCRIPTION OF THE INVENTION

Figure 1:
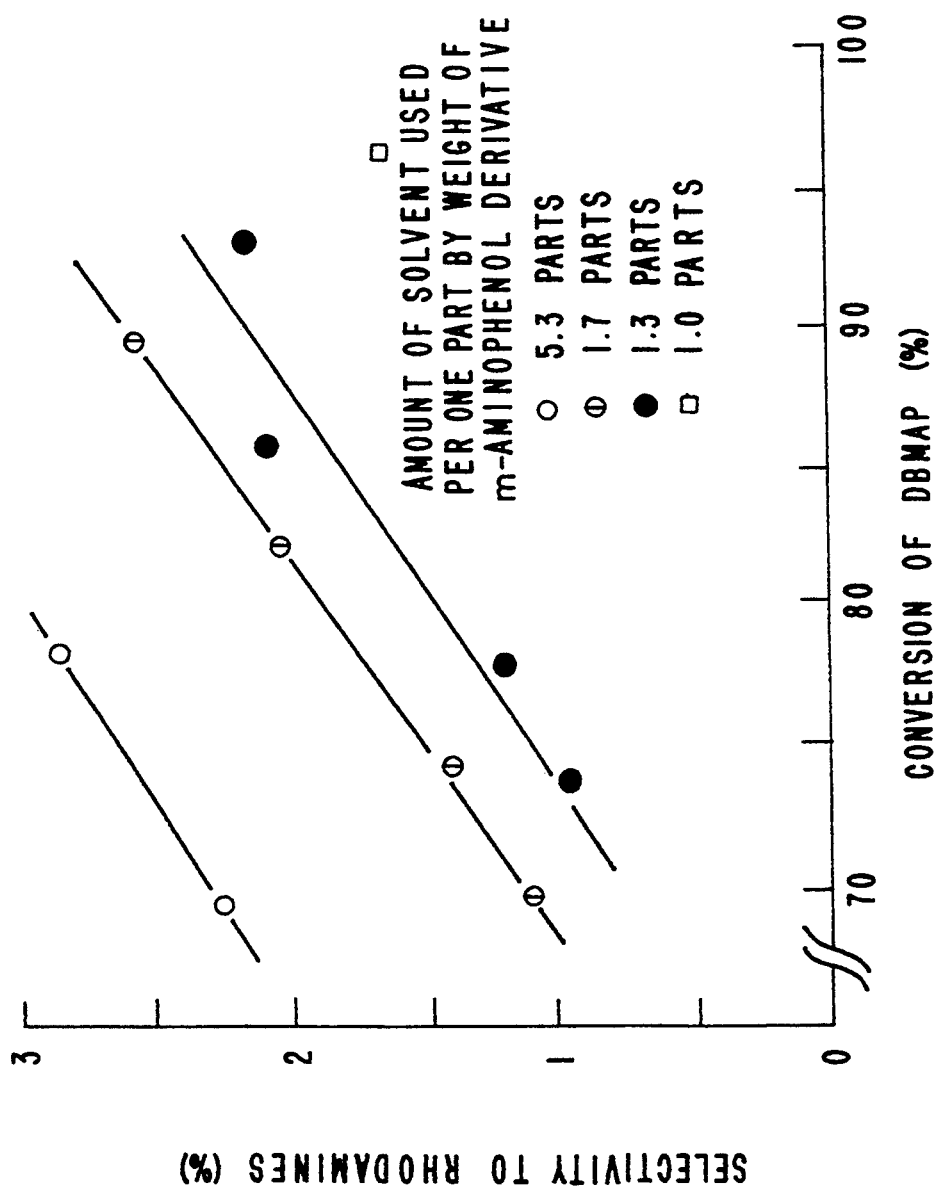
FIG. 1 shows the relation of selectivity of reaction to Rhodamines vs. the conversion of N,N-di-n-butyl-m-aminophenol (DBMAP) in which a varied amount of solvent is used.

The m-aminophenol wherein both $R^1$ and $R^2$ are alkyls of 1–6 carbons used in the invention includes, for example, N,N-dimethyl-m-aminophenol, N,N-diethyl-m-aminophenol, N,N-di-n-propyl-m-aminophenol, N,N-di-isopropyl-m-aminophenol, N,N-di-n-butyl-m-aminophenol, N-methyl-N-ethyl-m-aminophenol, N-ethyl-N-isopropyl-m-aminophenol, The m-aminophenol wherein one of $R^1$ and $R^2$ is a cycloalkyl of 4–8 carbons, preferably of 5–7 carbons, may be exemplified by N-ethyl-N-cyclohexyl-m-aminophenol.

For the reaction of the m-aminophenol derivative as above mentioned with phthalic anhydride, the latter is used usually in an amount of 0.7–2 moles per mole of the m-aminophenol derivative.

According to the invention, the reaction is effected in an amount of an organic solvent which is insufficient to dissolve the keto acid produced in the reaction, so that at least a portion of the keto acid produced in the reaction crystallizes out of the solvent and hence the reaction is allowed to proceed in a heterogeneous system or in a slurried state.

More specifically, it is particularly preferred that the solvent is used in an amount of 0.5–1.7 parts by weight in relation to one part by weight of the m-aminophenol derivative used. When the amount of solvent used is less than 0.5 parts by weight in relation to one part by weight of the m-aminophenol derivative used, the keto acid produced in the reaction crystallizes out of the solvent in an amount relatively too much in relation to the amount of the solvent used, so that the reaction mixture may not be stirred effectively, as it is important that the reaction mixture is effectively stirred in a large scale industrial production. In turn, when the amount of solvent used is more than 1.7 parts by weight in relation to one part by weight of the m-aminophenol derivative used, there is still produced a large amount of undesirable Rhodamine impurities in the reaction, and the yield of keto acid is reduced.

Strictly speaking, the amount of the solvent used is determined so that at least a portion of the keto acid as produced in the reaction crystallizes out of the solvent so that the reaction is allowed to proceed in a heterogeneous system or in a slurried state, namely in a dispersion of precipitates of keto acid in the solvent, and yet the reaction mixture may be effectively stirred.

The organic solvent used includes, for example, an aromatic hydrocarbon of 6–10 carbons such as benzene, toluene or xylene, an aliphatic hydrocarbon of 6–12 carbons such as octane, isooctane or decane, a halogenated hydrocarbon of 2–8 carbons, aliphatic, cycloaliphatic or aromatic, such as perchlene or chlorobenzene, ethers such as tetrahydrofuran, dibutyl ether or diphenyl ether, among which are especially preferred aromatic hydrocarbons or ethers.

By way of example, when the reaction of N,N-di-n-butyl-m-aminophenol with phthalic anhydride is carried out in an aromatic hydrocarbon such as benzene, toluene or xylene, the preferred amount of the solvent is in the range of 0.5–1.7 parts by weight, and the most preferred amount is 1.0–1.7 parts by weight, in relation to one part by weight of the N,N-di-n-butyl-m-aminophenol.

The reaction is effected at an elevated temperature, preferably at a temperature in the range of 60°–120° C. for a period of 4–40 hours, although the reaction temperature and time are not critical in the invention.

After the reaction, the reaction mixture is cooled usually to normal temperature, preferably to a temperature of 0°–35° C., most preferably to 10°–30° C., depending upon the solvent used, or a bad solvent such as a saturated hydrocarbon is added to the reaction mixture, to effect primary crystallization of the resultant keto acid, and the crude crystals are collected by filtration.

The primary crude crystals are then dissolved under heating in an aliphatic alcohol of 1–4 carbons or in a mixture of the aliphatic alcohol with water, and then cooled to effect secondary crystallization. The secondary crystallization may be effected at the same temperature range as in the primary crystallization. The secondary crystallization enables one to obtain a high purity keto acid which contains substantially no Rhodamine impurities.

There may be used as the alcohol for the secondary crystallization solvent, for example, methanol, ethanol, propanols such as isopropanol or butanols such as n-butanol. There may also be used a mixture of the alcohol with water, or a mixture of the alcohol with a hydrocarbon solvent, preferably an aromatic hydrocarbon of 6–10 carbons such as toluene or xylene, or an aliphatic hydrocarbon of 5–10 carbons such as pentane, hexane or heptane.

Further according to the invention, after the reaction, such an aliphatic alcohol of 1–4 carbons as hereinabove mentioned may be added to the reaction mixture and then the primary crystallization may be effected. The addition of the aliphatic alcohol to the reaction mixture enables selective dissolution of Rhodamines so that the reaction mixture in the form of slurry or dispersion is kept in a good state from which the resultant crystals can be collected by filtration easily.

The primary crude crystals may be dissolved in the alcohol under an elevated pressure, usually under a pressure of several atmospheric pressures, and then the solution may be cooled to effect the secondary crystallization.

As set forth above, the reaction of the m-aminophenol derivative with phthalic anhydride is carried out in a reduced amount of an organic solvent to allow at least a portion of the keto acid as it is produced in the reaction crystallizes out of the solvent so that the reaction is allowed to proceed in a heterogeneous state according to the invention. Thus, the by-production of undesirable Rhodamines by the reaction of the keto acid produced in the reaction with the m-aminophenol derivative used is substantially suppressed, thereby to improve the selectivity of the reaction to the keto acid.

Moreover, the resultant keto acid can be recovered in a high recovery rate simply by filtration, without resorting to such a method as alkali extraction, and there is obtained a high purity keto acid which contains substantially no Rhodamine impurities by effecting secondary crystallization of the resultant keto acid out of the alcohol.

Further according to the invention, the alcohol may be recovered from the secondary crystallization mother liquor, and if necessary, the alcohol is completely removed, to provide a residual solid which contains the keto acid. The solid is then dissolved in an inactive organic solvent which can be used as a reaction solvent, and the thus resultant solution may be added to the reaction mixture, and the mixture is then cooled to effect primary crystallization. This results in a remarkable improvement in yield of keto acid.

The amount of undesirable Rhodamines by-produced in the reaction is reduced according to the invention, and thus the ratio of the Rhodamines to the keto acid in the mother liquor after the secondary crystallization is very small. Therefore, according to the invention, the solvent in the mother liquor is exchanged with an organic solvent which can be used as a reaction solvent, and the resultant solution containing the keto acid can be advantageously used for primary crystallization together with the reaction mixture, thereby to increase the yield of the keto acid.

The invention will now be described in more detail with reference to examples, however, the invention is not limited to the examples.

EXAMPLE 1

An amount of 165 g (1.0 mole) of N,N-diethyl-m-aminophenol, 170.3 g (1.15 mole) of phthalic anhydride and 206 g of xylene (1.25 parts by weight in relation to one part by weight of the m-aminophenol) were placed in a reactor, and stirred for 7 hours at 115° C.

After about ten minutes from the start of the reaction, crystallization out of the solvent of the keto acid (4-N,N-diethylamino-2-hydroxy-2'-carboxybenzophenone) produced in the reaction began, and thereafter the crystallization continued and the reaction was allowed to proceed in a heterogeneous system until the completion of the reaction.

After the completion of the reaction, 247 g of xylene were added to the reaction mixture, and the mixture was cooled gradually to 20° C. to effect primary crystallization. The crude crystals of the keto acid were collected by filtration and washed with 577 g of n-butanol to provide 303.9 g (yield: 96.9%) of primary crude crystals.

An amount of 1486 g of n-butanol was added to the primary crude crystals and heated to dissolve the crystals therein, and then the mixture was cooled to 20° C. gradually. The resultant secondary crystals were collected by filtration and dried to provide 291.9 g of high purity keto acid (4-N,N-diethylamino-2-hydroxy-2'-carboxybenzophenone). The amount of Rhodamines in the keto acid was found to be not more than 0.1% by liquid chromatographic analysis. The yield was 93.1 mol %.

EXAMPLE 2

After the reaction, n-butanol was added to the reaction mixture in place of xylene, and otherwise in the same manner as in Example 1, primary crude crystals were obtained.

An amount of 1486 g of n-butanol was added to 303.6 g of the primary crude crystals and heated to dissolve the crystals therein, and then the mixture was cooled to 20° C. gradually to effect secondary crystallization. The resultant pale yellow crystals were collected by filtration and dried to provide 291.5 g of high purity keto acid (4-N,N-diethylamino-2-hydroxy-2'-carboxybenzophenone).

There were detected no Rhodamines in the keto acid by liquid chromatographic analysis. The yield was 93.5 mol %.

EXAMPLE 3

The reaction was effected in toluene in place of xylene, and after the reaction methanol was added in place of xylene to the reaction mixture, and the mixture was cooled gradually to 20° C. The primary crude crystals of the keto acid were collected by filtration and washed with methanol, and otherwise in the same manner as in Example 1.

An amount of 913 g of methanol was added to 304.5 g of the primary crude crystals and heated to 113° C. under a pressure of 3 Kg/cm$^2$ of nitrogen gas to completely dissolve the crystals therein, and then the solution was cooled to 20° C. gradually to effect secondary crystallization. The resultant pale yellow crystals were collected by filtration and dried to provide 295.3 g of high purity keto acid (4-N,N-diethylamino-2-hydroxy-2'-carboxybenzophenone).

There were detected no Rhodamines in the keto acid by liquid chromatographic analysis. The yield was 94.3 mol %.

EXAMPLE 4

An amount of 221 g (1.0 mole) of N,N-di-n-butyl-m-aminophenol, 177.7 g (1.2 mole) of phthalic anhydride and 191 g of xylene (0.86 parts by weight in relation to one part by weight of the m-aminophenol) were placed in a reactor, and stirred for 7 hours at 100° C.

After about one hour from the start of the reaction, crystallization of the keto acid (4-N,N-dibutylamino-2-hydroxy-2'-carboxybenzophenone) produced in the reaction began, and thereafter the crystallization continued and the reaction proceeded in a heterogeneous system until the completion of the reaction.

After the completion of the reaction, 191 g of xylene were added to the reaction mixture, and the mixture was cooled gradually to 20° C. The crude crystals were collected by filtration and washed with 70 g of xylene twice, to provide 320 g (yield: 86.6%) of primary crude crystals.

320 g of the crude crystals were added to 1250 g of methanol. The mixture was heated to dissolve the crystals in the methanol, and then the mixture was cooled to 20° C. gradually to effect recrystallization of the keto acid. The resultant crystals were collected by filtration and washed with 100 g of cold methanol twice, followed by drying the crystals to provide 255 g of high purity keto acid (4-N,N-di-n-butylamino-2-hydroxy-2'-carboxybenzophenone).

There were detected no Rhodamines in the keto acid by liquid chromatographic analysis. The yield was 69.0 mol %.

EXAMPLE 5

The reaction was effected in toluene in place of xylene, and otherwise in the same manner as in Example 4 to provide 258 g of high purity keto acid (4-N,N-di-n-butylamino-2-hydroxy-2'-carboxybenzophenone).

There were detected no Rhodamines in the keto acid by liquid chromatographic analysis. The yield was 69.8 mol %.

EXAMPLE 6

The crystals of keto acid (4-N,N-di-n-butylamino-2-hydroxy-2'-carboxybenzophenone) obtained in Example 4 were recrystallized, collected by filtration, and washed with cold methanol. The mother liquor was distilled to recover methanol.

An amount of 220 ml of xylene was added to the distillation bottom containing the keto acid to dissolve the keto acid therein.

The resultant solution was added to the same reaction mixture as obtained in Example 1 and then primary crystallization was effected, followed by working in the same manner as in Example 1, there were obtained 299 g of pale yellow crystals of high purity keto acid (4-N,N-di-n-butylamino-2-hydroxy-2'-carboxybenzophenone).

There were detected no Rhodamines in the keto acid by liquid chromatographic analysis. The yield was 81 mol % based on the N,N-di-n-butyl-m-aminophenol used.

EXAMPLE 7 AND COMPARATIVE EXAMPLE 1

An amount of 221 g (1.0 mole) of N,N-di-n-butyl-m-aminophenol, 177.7 g (1.2 mole) of phthalic anhydride and xylene in an amount indicated in FIG. 1 (parts by weight in relation to one part by weight of the m-aminophenol) were placed in a reactor, and stirred for 7 hours at 100° C. The relation of selectivity of reaction to Rhodamines vs. the conversion of the m-aminophenol is shown in FIG. 1.

When xylene was used in an amount of 5.3 parts by weight in relation to one part by weight of the m-aminophenol, the keto acid produced in the reaction remained completely dissolved in the solvent throughout the reaction. After completion of the reaction, the reaction mixture was cooled, and the thus crystallized keto acid was collected by filtration. The recovery rate was found to be 65%.

As illustrated in FIG. 1, when a reduced amount of solvent (1.7 parts, 1.3 parts or 1.0 part) was used so that at least a portion of the keto acid produced in the reaction crystallized out of the solution, the by-production of undesirable Rhodamines was remarkably reduced to provide a high purity keto acid.

As is further illustrated in FIG. 1, it is necessary that the selectivity of reaction to Rhodamines should be less than 3% in order to obtain a high purity keto acid in high yields after the secondary crystallization, and accordingly it is preferred that the solvent should be used in an amount of not more than 1.7 parts by weight in relation to one part by weight of the m-aminophenol used.

EXAMPLE 8

An amount of 207 g (1.0 mole) of N-ethyl-N-isoamyl-m-aminophenol, 177.6 g (1.2 mole) of phthalic anhydride and 300 g of diphenyl ether (1.5 parts by weight in relation to one part by weight of the m-aminophenol derivative used) were placed in a reactor, and stirred for 35 hours at 60° C.

After about 25 hours from the start of the reaction, the keto acid (4-N-ethyl-N-isoamylamino-2-hydroxy-2'-carboxybenzophenone) produced in the reaction began to crystallize out of the reaction mixture.

After completion of the reaction, it was found that the conversion of N-ethyl-N-isoamyl-m-aminophenol was 66%; the yield of keto acid (4-N-ethyl-N-isoamylamino-2-hydroxy-2'-carboxybenzophenone) was 65%; and the yield of Rhodamines was 1%.

The thus obtained reaction mixture was cooled to 30° C. and 230 g of the primary crude crystals of keto acid were collected by filtration (yield: 64.8%). An amount of 1700 ml of a mixture of methanol/water (75/25 in a volume ratio) was added to the primary crude crystals and heated to dissolve the crystals therein. The mixture was then cooled gradually to 20° C. to effect recrystallization and the resultant crystals were collected by filtration.

The amount of Rhodamines in the keto acid was found to be not more than 0.1% by liquid chromatographic analysis.

What is claimed is:

1. In a method of producing a keto acid having the general formula

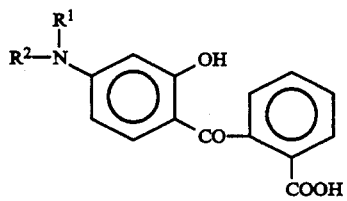

wherein $R^1$ and $R^2$ independently represent an alkyl of 1–6 carbons or a cycloalkyl of 4–8 carbons, by reacting an m-aminophenol having the general formula

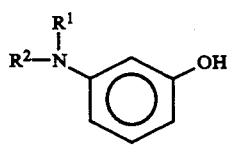

wherein $R^1$ and $R^2$ are the same as above, with phthalic anhydride, in an organic solvent, the improvement comprising effecting the reaction in the organic solvent in an amount of from 0.5 to 1.7 parts by weight organic solvent per one part by weight of the m-aminophenol, so that at least a portion of the resultant keto acid crystallizes out of the solvent and allowing the reaction to proceed in a heterogenous system.

2. The improvement as claimed in claim 1 wherein the organic solvent is benzene, toluene or xylene.

3. The improvement as claimed in claim 1 wherein the organic solvent is diphenyl ether.

4. The improvement as claimed in claim 1 wherein the m-aminophenol is N,N-diethyl-m-aminophenol, N,N-dibutyl-m-aminophenol or N-ethyl-N-isoamyl-m-aminophenol.

5. The improvement as claimed in claim 4 wherein after the reaction, an aliphatic alcohol of 1–4 carbons is added to the reaction mixture, and then the primary crystallization is effected.

6. In a method of producing a keto acid having the general formula

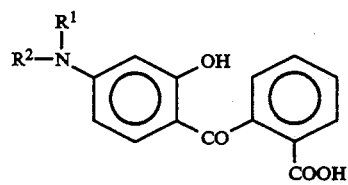

wherein $R^1$ and $R^2$ independently represent an alkyl of 1–6 carbons or a cycloalkyl of 4–8 carbons, by reacting an m-aminophenol having the general formula wherein $R^1$ and $R^2$ are the same as above, with phthalic anhydride, in an organic solvent, the improvement comprising:

(a) effecting the reaction in the organic solvent in an amount of from 0.5 to 1.7 parts by weight organic solvent per one part by weight of the m-aminophenol, so that at least a portion of the resultant keto acid crystallizes out of the solvent and allowing the reaction to proceed in a heterogenous system;

(b) cooling the resultant reaction mixture to effect primary crystallization to provide crude crystals of the keto acid;

(c) dissolving the primary crude crystals in an aliphatic alcohol of 1–4 carbons, or a mixture of the alcohol with water, or a mixture of the alcohol with a hydrocarbon solvent;

(d) effecting secondary crystallization from the solution of step (c);

(e) recovering the solution of step (c) from the resultant crystallization mother liquor; and (f) adding the recovered keto acid to the reaction mixture for use in the primary crystallization.

7. The improvement as claimed in claim 6 wherein the aliphatic alcohol is methanol or butanol.

8. The improvement as claimed in claim 5 wherein the aliphatic alcohol is methanol or butanol.

9. The improvement as claimed in claim 6 wherein the hydrocarbon solvent is an aromatic hydrocarbon of 6–10 carbons.

10. The improvement as claimed in claim 6 wherein the hydrocarbon solvent is an aliphatic hydrocarbon of 5–10 carbons.

11. The improvement as claimed in claim 9 wherein the aromatic hydrocarbon is toluene or xylene.

12. The improvement as claimed in claim 10 wherein the aliphatic hydrocarbon is hexane.

13. The improvement as claimed in claim 6 wherein the crude crystals are dissolved in the alcohol or the mixture under an elevated pressure.

14. The improvement as claimed in claim 6 wherein the reaction is effected at a temperature in the range of 60°–120° C.

15. The improvement as claimed in claim 6 wherein the m-aminophenol is N,N-diethyl-m-aminophenol, N,N-dibutyl-m-aminophenol or N-ethyl-N-isoamyl-m-aminophenol.

* * * * *